(12) United States Patent
Kim et al.

(10) Patent No.: US 7,838,047 B2
(45) Date of Patent: Nov. 23, 2010

(54) **PHARMACEUTICAL COMPOSITION AND HEALTH FOOD COMPRISING EXTRACT OF *PHELLINUS* SP. PL3 OR PHELLINSIN A ISOLATED FROM THE SAME AS AN EFFECTIVE COMPONENT FOR PREVENTION AND TREATMENT OF CARDIOVASCULAR DISEASE**

(75) Inventors: Sung Uk Kim, Daejeon (KR); Eui Il Hwang, Daejeon (KR); Ju Ryoung Kim, Daejeon (KR); Tae Sook Jeong, Daejeon (KR); Sangku Lee, Daejeon (KR); Sang Han Lee, Daejeon (KR); Jae Sun Moon, Daejeon (KR); Mun-Chual Rho, Daejeon (KR)

(73) Assignee: Korea Research Institute of Bioscience and Biotechnology, Daejeon (KR)

( * ) Notice: Subject to any disclaimer, the term of this patent is extended or adjusted under 35 U.S.C. 154(b) by 147 days.

(21) Appl. No.: 12/204,950

(22) Filed: Sep. 5, 2008

(65) Prior Publication Data

US 2009/0005440 A1 Jan. 1, 2009

Related U.S. Application Data

(63) Continuation of application No. 11/290,283, filed on Nov. 30, 2005, now abandoned.

(30) Foreign Application Priority Data

Nov. 30, 2004 (KR) .................. 10-2004-0099339

(51) Int. Cl.
*A01N 65/00* (2009.01)
(52) U.S. Cl. ................................... 424/725
(58) Field of Classification Search ............. None
See application file for complete search history.

(56) References Cited

FOREIGN PATENT DOCUMENTS

| KR | 1020010008884 | | 2/2001 |
|----|---------------|---|--------|
| KR | 2001069898 | * | 7/2001 |

OTHER PUBLICATIONS

David L. Nelson, et al. Lehninger Principles in Biochemistry, lipid biosynthesis, 2000, 770-817.
Daniel Steinberg, et al., 3rd Edition, 2000 Worth Publishers, New York; N. Engl. J. Med., "Beyond Cholesterol, Modifications of Low-Density Lipoprotein That Increase Its Atherogenicity", 1989, 320, 915-924.
Charles R. Cannan, et al. Circulation, American Heart Association, Natural History of Hypertrophic Cardiomyopathy, 1995, 92, 2488-2496.
Peter Wagner, et al. Arterioscler. Thromb. Vase. Biol., 1997, 17, "Copper Ions Promote Peroxidatin of Low Density Lipoprotein Lipid by Binding to Histidine Residues of Apolipoprotein B100, But They Are Reduced at Other Sites on LDL", 3338-3346.
Masa-aki Kawashiri, et al., Curr. Atheroscler. Res., 2000, 2, High-Density Lipoprotein Metabolism; Molecular Targets for New Therapies for Atherosclerosis, pp. 363-363.
Eva Hurt Camejo, et al., "Phospholipase $A_2$ in Vascular Disease" Circ. Res. 2001, 89, 298-304.
Yun Seong Song, et al., "Anti-angiogenic, Antioxidant and Xanthine Oxidase Inhibition Activities of the Mushroom Phellinus Linteus", J. Ethnopharmacol., 2003, 88, 113-116.
Eui-Il Hwang, et al., "Phellinsin A, a Novel Chitin Syunthases Inhibitor Produced by *Phellinus* sp. PL3", J. Antibiotcs., 2000, 9, 903-911.
Larsen and Cobb's group III, Synopsis Fungorum 3: Phellinus (Hymenochaetaecae)—A survey of the world taxa. p. 206, Fungiflora, Oslo, Norway, 1990.
Y. C. Dai and M. Q. Xu: Studies on the medicinal polypore, Phellinus baumii, and its kim, P. linteus, Mycotaxon 62, 191-200, 1998.
Ryuichi Mashima, et al. Curr Opin Lipidol., 2001, 12, 411-18.

* cited by examiner

*Primary Examiner*—Michael V Meller
(74) *Attorney, Agent, or Firm*—Frommer Lawrence & Haug LLP; Ronald R. Santucci

(57) ABSTRACT

The present invention relates to a pharmaceutical composition and health food comprising *Phellinus* sp. PL3 extract or phellinsin A isolated from the same as an effective component. More particularly, the present invention relates to a pharmaceutical composition and health food comprising *Phellinus* sp. PL3 extract or phellinsin A isolated from the same as an effective component, wherein the *Phellinus* sp. PL3 extract and its phellinsin A inhibit the oxidation of low density lipoprotein (LDL), and further, they can be used as a component for medicine and food to effectively prevent and treat cardiovascular diseases such as hyperlipemia and arteriosclerosis.

13 Claims, 1 Drawing Sheet

US 7,838,047 B2

PHARMACEUTICAL COMPOSITION AND HEALTH FOOD COMPRISING EXTRACT OF *PHELLINUS* SP. PL3 OR PHELLINSIN A ISOLATED FROM THE SAME AS AN EFFECTIVE COMPONENT FOR PREVENTION AND TREATMENT OF CARDIOVASCULAR DISEASE

CROSS REFERENCE TO RELATED APPLICATION

This application is a continuation of U.S. patent application Ser. No. 11/290,283 filed Nov. 30, 2005 now abandoned and is based on, and claims priority from Korean Patent Application No. 10-2004-0099339, filed on Nov. 30, 2004, the disclosures of which are hereby incorporated by reference.

BACKGROUND OF THE INVENTION

1. Field of the Invention

The present invention relates to a pharmaceutical composition and health food comprising *Phellinus* sp. PL3 extract or phellinsin A isolated from the same as an effective component. More particularly, the present invention relates to a pharmaceutical composition and health food comprising *Phellinus* sp. PL3 extract or phellinsin A isolated from the same as an effective component, wherein the *Phellinus* sp. PL3 extract and its phellinsin A inhibit the oxidation of low density lipoprotein (LDL). Further, they can be used as active ingredients for manufacturing medicines and food to prevent and treat cardiovascular diseases such as hyperlipemia and arteriosclerosis.

2. Background of the Related Art

Cardiovascular diseases such as arteriosclerosis have become more popular among adults recently due to increasing stress, unregular and excessive dietary habits, air pollution and the like. The gain of cholesterol, especially low-density lipoprotein (LDL)-cholesterol, has been recognized as a major cause of arteriosclerosis and its related diseases. Therefore, as a way of prevent the above diseases, there have been efforts to decrease the level of low-density lipoprotein (hereinafter, referred to as "LDL") in body by suppressing the absorption of cholesterol and inhibiting its biosynthesis [Principles in Biochemistry, lipid biosynthesis, 770-817, 3rd Edition, 2000 Worth Publishers, New York; Steinberg, N. Engl. J. Med., 1989, 320: 915-924].

Currently, oxidized LDL products, being a cause of arteriosclerosis, produced in blood have drawn much attention [Circulation, 1995, 91: 2488-2496; Arterioscler. Thromb. Vasc. Biol., 1997, 17: 3338-3346]. Especially, it has been reported that LDL is structurally modified by the excessive oxidation into highly modified LDL (HM-LDL), which is then introduced into a macrophage to generate foam cells. As a result, many lines of active and extensive studied have been conducted to identify the factors involved in production and removal of LDL peroxides [Curr. Atheroscler. Rep., 2000, 2: 363-372]. The formation of plague inside the wall of a blood vessel wall and its rupture is a major cause to bring about myocardial infarction. Arteriosclerosis, a kind of chronic inflammatory process that occurs in response to an injury in the wall of a blood vessel, is suggested to be a defensive mechanism rather than an injury mechanism [Circ. Res. 2001, 89: 298-304].

Traditionally, probucol, N,N'-diphenylenediamine, butylated hydroxyanisol (BHA) and butylated hydroxy toluene (BHT) as a phenolic synthetic anti-oxidant and the like have been administered to treat hyperlipemia. These medicines are advantageous in that they have anti-oxidative activity sufficient to decrease the level of LDL cholesterol in blood, reduce the degree of oxidation and the formation of lesions. However, they are known to have a few adverse actions and thus have been limited in their administration. Accordingly, there has been a growing concern on the combined therapeutic method for injecting a LDL anti-oxidant together with a lipid reducer in treating patients of hyperlipemia or arteriosclerosis. Hence, it is in urgent need to develop an anti-oxidant with an excellent anti-oxidative capability without any side effects.

*Phellinus* sp. PL3 is a mushroom belonging to Subphylum Basidiomtcotina, Order Aphyllophorales, Class Hymenochaetaceae, Genus *Phellinus* Quel. em. Imax. Further, *Phellinus linteus* has been reported to have several pharmaceutical efficacies enhancing immune responses, activating gastric functions, detoxifying and the like. Especially, *Phellinus linteus* is known to have a relatively high inhibitory activity against tumors from the animal experiments. Further, it was recently known that *Phellinus linteus* has anti-angiogenic, ant-oxidative, and inhibitory activities against xanthine oxidase and the like [J. Ethnopharmacol., 2003, 88: 113-116]. However, the above study has merely compared *Phellinus linteus* extract with vitamin C, thereby clarifying that *Phellinus linteus* extract scavenges free radicals and inhibits lipid peroxidation. Therefore, it is discriminated in its content from that of the present invention.

Further, *Phellinus* sp. PL3 extract or phellinsin A has been known to highly inhibit chitin synthase 2 of *Saccharomyces cerevisiae* producing chitin as a constituent of cell wall in fungi [J. Antibiotics, 2000, 9: 903-911]. Meanwhile, the present inventors have obtained a patent titled "Novel compound phellinsin A inhibiting chitin synthase 2 and pharmaceutical composition for an anti-fungal agent comprising the same [Korean Pat. No. 316010].

SUMMARY OF THE INVENTION

The inventors of the present invention have made extensive efforts to find a natural product which meets the practical requirement as an LDL anti-oxidant by screening various natural products. As a consequence, they have discovered that *Phellinus* sp. PL3 extract or phellinsin A isolated from the same inhibits the oxidation of low density lipoprotein (LDL). Further, they can be used in manufacturing a pharmaceutical drug and health food comprising *Phellinus* sp. PL3 extract or phellinsin A as an effective component useful in prevention and treatment of cardiovascular diseases such as hyperlipemia and arteriosclerosis, thereby completing the present invention.

Therefore, in one aspect, the present invention provides a pharmaceutical composition comprising *Phellinus* sp. PL3 extract or phellinsin A isolated from the same as an effective component useful in prevention and treatment of cardiovascular diseases.

In another aspect, the present invention provides health food comprising *Phellinus* sp. PL3 extract or phellinsin A isolated from the same as an effective component.

BRIEF DESCRIPTION OF THE DRAWINGS

The above and other objects, features and other advantages of the present invention will be more clearly understood from the following detailed description taken in conjunction with the accompanying drawing, in which.

DETAILED DESCRIPTION OF THE PREFERRED EMBODIMENT

Figure 1:
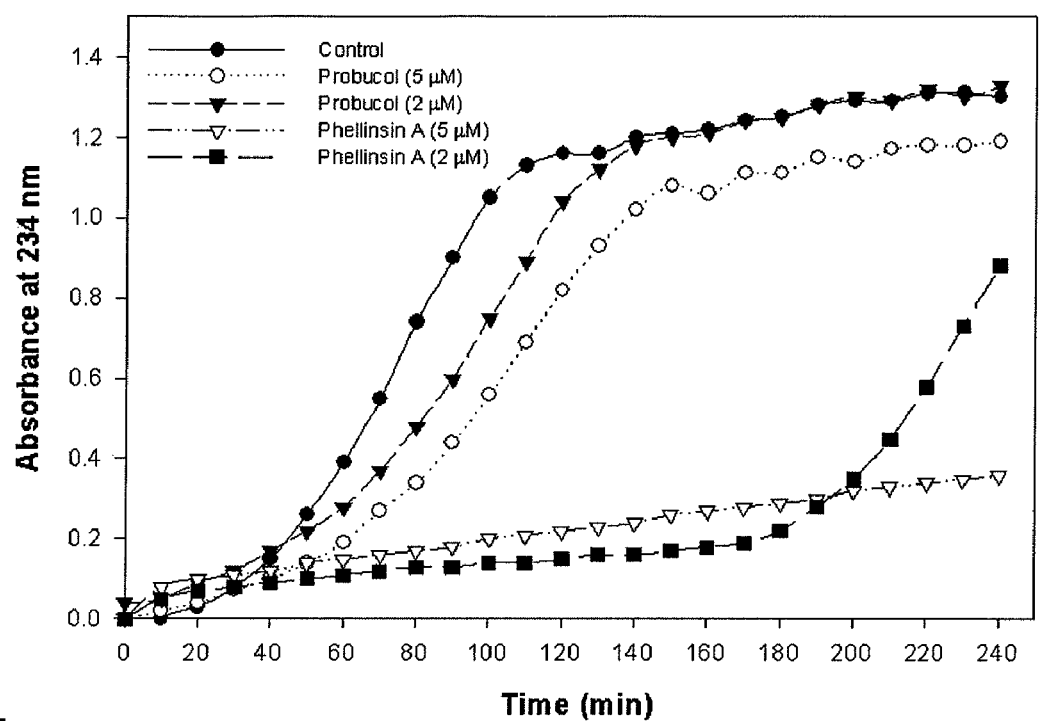
FIG. 1 depicts the anti-oxidant activity of phellinsin A to low-density lipoprotein by measuring the absorbance.

Hereinafter, the present invention will be described in greater detail as set forth hereunder.

The present invention relates to a pharmaceutical composition and health food comprising *Phellinus* sp. PL3 extract or phellinsin A isolated from the same as an effective component. More specifically, the present invention relates to a pharmaceutical composition and health food comprising *Phellinus* sp. PL3 extract or phellinsin A isolated from the same as an effective component, wherein the *Phellinus* sp. PL3 extract and its phellinsin A can inhibit the oxidation of low density lipoprotein (LDL), and further, they can be used for manufacturing a pharmaceutical drug and health food to prevent and treat cardiovascular diseases such as hyperlipemia and arteriosclerosis.

The chemical structure of phellinsin A of the present invention is represented by the following Formula 1 shown below.

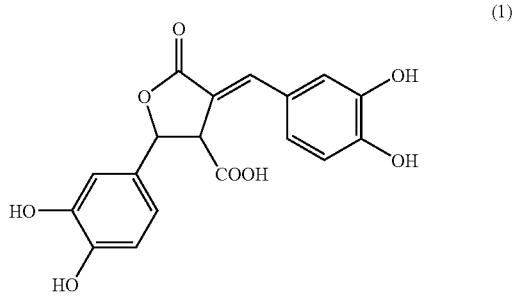

(1)

The compound phellinsin A of Formula 1, a phenol compound containing γ-lactone, can be used alone itself or in the form of a pharmaceutically acceptable salt, and shall include all its salts, hydroxides and solvated compounds prepared by conventional methods.

The *Phellinus* sp. PL3 extract or phellinsin A isolated from *Phellinus* sp. PL3 in the present invention can be prepared by all conventional processes. The compound phellinsin A can be isolated from *Phellinus* sp. PL3 and also synthesized by conventional methods of organic synthesis.

The *Phellinus* sp. PL3 extract or phellinsin A isolated from the same of the present invention is extracted, separated and purified as follows.

Above all, the fermented broth of *Phellinus* sp. PL3 is extracted with an organic solvent. Preferably, the solvent for extraction can be at least one selected from the group comprising water, alcohols, ethyl acetate, chloroform and acetone. In detail, the culture broth of *Phellinus* sp. PL3 is added to ethyl acetate, extracted and concentrated under reduced pressure to produce a crude extract. The resulting crude extract is separated twice by performing a silica gel column chromatography using a chloroform-methanol mixture as an eluent. Preferably, the ratio between chloroform and methanol in the eluent should be adjusted in the range of from 90:10 (v/v) to 80:20 (v/v), and more preferably, to 80:20 (v/v) primarily and to 90:10 (v/v) secondarily. Then, the fraction having an inhibitory activity is concentrated under reduced pressure, separated again by performing a reversed phase silica gel column chromatography using a methanol-water mixture as an eluent. Preferably, the ratio of methanol and water in the eluent can be adjusted in the range of from 60:40 (v/v) to 50:50 (v/v), and more preferably, to 50:50 (v/v).

Then, the active fraction is separated and purified by using a preparative TLC to produce a partially-purified active material. Preferably, the solvent can be a mixed solvent of chloroform, methanol and acetone. More preferably, the ratio in the solvent can be adjusted in the range of 85-90:7-8:2-3, and most preferably, to 90:7.5:2.5 (v/v). Then, the partially-purified active fraction is separated by performing high performance liquid chromatography (HPLC) using a methanol-water mixture as an eluent. Preferably, the ratio of methanol and water can be adjusted in the range of 30:70 to 20:80 (v/v), and more preferably, to 20:80 (v/v). By the above-mentioned procedure, the compound phellinsin A can be separated with more than 90% of purity, and finally purified by performing a preparative TLC to produce pure phellinsin A. Preferably, the mixed solvent of methanol and water can be adjusted in the ratio range of from 30:70 to 20:80, and more preferably, to 20:80 (v/v). In the present invention, pure compound phellinsin A can be obtained in a yield of 600 μg/L from the culture broth of *Phellinus* sp. PL3.

The *Phellinus* sp. PL3 extract or phellinsin A isolated from the same has the anti-oxidative activity to LDL. The *Phellinus* sp. PL3 extract and its phellinsin A can be applied usefully to prevent and treat cardiovascular diseases such as hyperlipemia and arteriosclerosis.

The pharmaceutical composition comprising *Phellinus* sp. PL3 extract or phellinsin A isolated from the same of the present invention further comprises one or more of effective components having the same or similar function.

In addition, the pharmaceutical composition of the present invention further comprises one or more of pharmaceutically acceptable carriers in order to be administered. Preferably, the pharmaceutically acceptable carrier can include saline, sterilized water, Ringer's solution, buffered saline, dextrose solution, malto-dextrin solution, glycerin, ethanol and their combination. Depending upon a desired use, other conventional additives including an anti-oxidant, a buffer solution, an anti-fungal agent or the like can be used. In addition, the pharmaceutical composition of the present invention can further comprise a diluent, a disperse agent, a surfactant, a binder and a lubricant. The pharmaceutical composition suitable for administration can be injections such as solutions, suspensions, elixirs and the like, pills, capsules, granules or tablets. Further, other methods suitable for preparation disclosed in this art or described in Remington's Pharmaceutical Science (Mack Publishing Company, Easton Pa.) can be also used.

The pharmaceutical composition of the present invention can be parenterally administered (including intravenous, subcutaneous, peritoneal or lesional); or orally administered depending upon the desired use.

The dosage of the substance of the invention will vary depending on factors such as body weight, age, sex, physical conditions, diets, administration period, administration method, discharge ratio and severeness of diseases of patients, etc.

In the *Phellinus* sp. PL3 extract, the daily dose can be preferable to be in the range of from 800 to 2,000 mg/kg, more preferable from 1,000 to 1,500 mg/kg. In the compound phellinsin A, the daily dose can be preferable in the range of from 0.1 to 100 mg/kg, more preferable in the range of from 0.5 to 10 mg/kg.

The pharmaceutical composition of the present invention can be administered to prevent and treat cardiovascular diseases, alone or in combination with surgery, hormone treatment, a drug and a biological controller.

The composition of the present invention can be used as an additive for health food in order to improve cardiovascular diseases. The *Phellinus* sp. PL3 extract and the compound phellinsin A isolated form the same can be used as a food additive alone or in combination with other foods or food constituents via conventional procedures and contents suitable for foods. Depending upon a desired use (prevention, health management or treatment), the combination of effective constituents can be adjusted in their ratio. Preferably, the *Phellinus* sp. PL3 extract or the phellinsin A isolated form the same can be added in a ratio of from 1 to 20 wt parts per 100 wt parts of total source composition, and more preferably in the ratio of from 5 to 10 wt parts per 100 wt parts of total source composition. For a long-term administration, this content can be adjusted below the above range by considering health conditions, hygienic conditions or health control, or more than the above range because the effective component is proven safe.

The composition of the present invention is not limited but can be added practically to any kind of foods including meat, sausage, bread, chocolate, candy, snack, cookie, pizza, ramyun, other noodles, gums, diary products such as ice cream, soup, drinks, teas, alcohols and vitamin complexes.

The health drink composition of the present invention can further comprise various sweetening agents or natural carbohydrates, as is the case with conventional drinks. Preferably, the natural carbohydrate can include monosaccharides such as glucose and fructose, di-saccharides such as maltose and sucrose, polysaccharides such as dextrin and cyclodextrin, and sugar alcohols such as xylitol, sorbitol and erythritol. The sweetening agent can include natural substances such as thaumatin and stevioside and synthetic substances such as saccharin and aspartame. Preferably, the natural carbohydrate can be added in the ratio of from 0.01 to 0.04 g per 100 mL of the present composition, and more preferably, in the ratio of from 0.02 to 0.03 g.

The composition of the present invention can further comprises various nutrients, vitamin, electrolytes, flavoring agents or coloring agents and pectic acids and its salts, alginic acid and its salts, protective colloids, viscosity enhancers, pH controllers, stabilizers, preservatives, glycerin, alcohols, carbonating agents for carbonated drinks. Further, the composition of the present invention can include fresh flesh to manufacture natural fruit juices, fruit juice drinks and vegetable drinks. The constituents mentioned above can be used independently or in combination. Generally, the additive can be often added in the ratio of from 0.01 to 0.1 wt parts per 100 wt parts of the present composition, but not limited.

EXAMPLES

Practical and presently preferred embodiments of the present invention are illustrated as shown in the following Examples.

However, it will be appreciated that those skilled in the art, in consideration of this disclosure, may make modifications and improvements within the spirit and scope of the present invention.

Example 1

Selection and Identification of Phellinsin A-Producing Strain

The phellinsin A-producing mushroom, strain PL3, having a fruiting body and pale yellow color was collected from the trunk of *Morus alba* at Kyeryong Mountain, Chungcheongnam Province, Korea. For the evaluation of cultural characteristics, the strain was grown on Czapak media (0.2% $NaNO_3$, 0.1% $K_2HPO_4$, 0.05% $MgSO_4.7H_2O$, 0.05% KCl, 0.001% $FeSO_4.7H_2O$, 3.0% sucrose, 1.5% agar), MEA media (2.5% yeast extract, 1.5% agar), CYA media (0.5% yeast extract, 0.3% $NaNO_3$, 0.1% $K_2HPO_4$, 0.05% $MgSO_4.7H_2O$, 0.05% KCl, 0.001% $FeSO_4.7H_2O$, 0.0005% $CuSO_4.5H_2O$, 0.001% $ZnCl_2.7H_2O$, 3.0% sucrose, 1.5% agar), CYA 20S media (0.5% yeast extract, 0.3% $NaNO_3$, 0.1% $K_2HPO_4$, 0.05% $MgSO_4.7H_2O$, 0.05% KCl, 0.001% $FeSO_4.7H_2O$, 0.0005% $CuSO_4.5H_2O$, 0.001% $ZnCl_2.7H_2O$, 20.0% sucrose, 1.5% agar), PDA media (Difco Co., product No.: 0013-17-6) and YMA media, for 14 days at 25 to 42° C.

As a result, the resulting the strain PL3 was observed to proliferate best at 30° C. and stopped to grow at a temperature higher than 42° C. Besides, the strain PL3 proliferated rapidly in MEA, PDA and YMA media, but grew very slowly in Czapek, CYA and CYA20S media. In all 6 different kinds of media, the strain PL3 showed the same yellow color. Then, the mycelium became keratinized gradually according to time passage. Based on the morphological and biochemical characteristics, strain PL3 was classified into *Phellinus* species owing to abundant hymenial setae, blackening of their basidiocarps to KOH treatment, and dimitic hyphal structures. The combination of morphological and biochemical characteristics of basidiospores, setae, basidiocarps and host specificity lead to the conclusion that *Phellinus* sp. PL3 strain of the present invention is closely related to *Phellinus linteus*, *Phellinus baumi* or *Phellinus johnsonianus* and the like. However, strain PL3 is slightly different from the above three strains [Larsen, M. J. and L. A. Cobb-Poulle, Synopsis Fungorum 3: *Phellinus* (Hymenochaetaceae)—A survey of the world taxa, p. 1-154, Fungiflora, Oslo, Norway, 1990]. *Phellinus johnsonianushwas* has been reported to be resupinate to reflexed in the morphology of basidiocarps, while strain PL3 is distinctly sessile. Strain PL3 was consistent with description on *Phellinus baumii* according to Dai and Xu [Y. C. Dai and M. Q. Xu: Studies on the medicinal polypore, *Phellinus baumii*, and its kin, *P. linteus*, Mycotaxon, 67: 191-200, 1998], concerning the thickness in KOH solution of tramal skeletal hyphae. Tramal skeletal hyphae were 2.3-4.8 μm thick in strain PL3, 2.5-3.5 μm in *Phellinus baumi* and 3.9-6.0 μm in *Phellinus linteus*. However, this strain had a little larger basidiopores (4.3-5.5×3.8-4.8 μm) than that of *Phellinus baumii* (3.3-4.5×2.4-3.5 μm) according to Dai and Xu descriptions [Y. C. Dai and M. Q. Xu Studies on the medicinal polypore, *Phellinus baumii*, and its kin, *P. linteus*, Mycotaxon, 67: 191-200, 1998]. Size of basidiospores in strain PL3 was similar to that of *Phellinus linteus*. In addition, the contextural skeletal hyphae were thinner than those of *Phellinus linteus* and *Phellinus baumii*. The contextural skeletal hyphae in KOH solution were 2.4-4.1 μm thick in strain PL3, while they were in the range of 4.5-6.1 μm in *Phellinus linteus* and 4.8-7.0 μm in *Phellinus baumii*, respectively.

As a consequence, the strain PL3 isolated in the present invention seems to be a relative but a distinctly different species of the *Phellinus* species. Therefore, the fungus PL3 of the present invention was designated as *Phellinus* sp. PL3 and deposited in the International Deposit Organization, the Korean Collection for Type Culture (KCTC) on May 17, 1999 (accession number: KCTC 0613 BP).

Example 2

Cultivation of *Phellinus* sp. PL3

One frozen stock vial (1 mL of spore suspension in 10% glycerol, −80° C. freezer) of *Phellinus* sp. PL3 strain was inoculated in 50 mL of seed culture medium (glucose 0.5%, soluble starch 1.5%, yeast extract 0.2%, polypeptone 0.5%, KH$_2$PO$_4$ 0.1%, MgSO$_4$.7H$_2$O 0.05%, pH 5.9 prior to autoclaving) contained in 500 mL flask, and then, cultivated at 26° C. for 4 days. Twenty mL of the seed culture was transferred into a 5-Liter baffled-flask containing 1 L of PDA medium (purchased from Difco Co. Ltd., product No. 0013-17-6). The fermentation was carried out for 5 days at 26° C. on a rotary shaker at 150 rpm.

Example 3

Preparation of Methanol Extract of *Phellinus* sp. PL3

10 L of culture broth of *Phellinus* sp. PL3 obtained in Example 2 was added to the same volume of methanol, extracted twice and concentrated under reduced pressure to produce a solvent extract in an oilic form.

Example 4

Preparation of Methanol and Ethyl Acetate Extract of *Phellinus* sp. PL3

10 L of culture broth of *Phellinus* sp. PL3 obtained in Example 2 was added to the same volume of methanol, extracted twice and concentrated under reduced pressure to produce a solvent extract in an oilic form. Then, the resulting extract was extracted twice by using ethyl acetate to produce a solvent extract in an oil state.

Example 5

Preparation of Ethyl Acetate Extract of *Phellinus* sp. PL3

10 L of culture broth of *Phellinus* sp. PL3 obtained in Example 2 was added to the same volume of ethyl acetate, extracted twice and concentrated under reduced pressure to produce a solvent extract in an oilic form.

Example 6

Purification of Phellinsin A From *Phellinus* sp. PL3 Strain

10 L of culture broth of *Phellinus* sp. PL3 obtained in Example 2 was added to the same volume of ethyl acetate, extracted twice and concentrated under reduced pressure to produce a crude extract. Then, the crude extract was separated twice by performing a silica gel column chromatography using a chloroform-methanol mixture as an eluent. At this moment, the ratio of chloroform and methanol in the eluent was adjusted to 80:20 (v/v) primarily, and 90:10 (v/v) secondarily. Then, the fraction having an inhibitory activity was concentrated under reduced pressure, separated twice by performing a reverse phase silica gel column chromatography using a methanol-water mixture as an eluent. At this moment, the ratio of methanol and water in the eluent was adjusted to 50:50 (v/v).

Then, the active fraction was again separated and purified by using a preparative TLC to produce a partially-purified active material. At this moment, a mixed solvent of chloroform, methanol and acetone was utilized and the ratio in the solvent was adjusted to 90:7.5:2.5 (v/v). Then, the partially-purified active fraction was separated by performing high performance liquid chromatography (HPLC) using a methanol-water mixture as an eluent. At this moment, the ratio of methanol and water was adjusted to 20:80 (v/v). By the above-mentioned procedure, phellinsin A was separated with more than 90% of purity, and finally purified by using a preparative TLC to produce pure phellinsin A. At this moment, a mixed solvent of methanol and water was utilized as a solvent in a ratio adjusted to 20:80 (v/v). As a result, pure phellinsin A was obtained in 600 μg per liter.

For the *Phellinus* sp. PL3 extract or phellinsin A isolated from the same prepared by the procedure as described in Examples, in order to identify the anti-oxidative activity, the following experiment will be accomplished as described in Experimental Examples.

Experimental Example 1

Experiment of Anti-Oxidation to LDL by TBARS Method

The *Phellinus* sp. PL3 extract and the phellinsin A isolated from the same prepared as described in Examples were examined for their anti-oxidant activity to LDL as follows.

$Cu^{2+}$ is reported to induce $Cu^{2+}$-mediated LDL-oxidation. In the present invention, dialdehydes as an oxidative product of unsaturated fatty acids was measured by performing TBARS (thiobarbituric acid-reactive substances) method to investigate the anti-oxidant activities of *Phellinus* sp. PL3 extract and the phellinsin A isolated from *Phellinus* sp PL3.

300 mL of human plasma was centrifuged at 100,000×g for 24 hours with an ultracentrifuge to remove a very low density lipoprotein (VLDL)/chylomicron layer floated on the supernatant. The remaining solution was adjusted to 1.063 g/mL of gravity and centrifuged at 100,000×g for 24 hours to separate again 25 mL (1.5-2.5 mg protein/mL) of LDL floated on the supernatant. Then, 20 μL of LDL separated above (50-100 μg/mL of protein concentration) was mixed with 210 μL of 10 mM PBS buffer and added with 10 μL of *Phellinus* sp. PL3 extract and the phellinsin A isolated from *Phellinus* sp. PL3 of the present invention, respectively. At this moment, *Phellinus* sp. PL3 extract and the phellinsin A isolated from *Phellinus* sp. PL3 was dissolved in DMSO (dimethylsulfoxide) and diluted several times before used for the experiment. As a negative control, only solvent was added, while as a positive control, probucol was added before use (Curr Opin Lipidol., 2001, 12: 411-18).

Then, 10 μL of 0.25 mM CuSO$_4$ was added to the resulting solution, reacted at 37° C. for 4 hours and added with 1 mL of 20% trichloroacetic acid (TCA) solution to stop the reaction. Then, 1 mL of 0.67% TBA solution dissolved in 0.05 N NaOH was added, stirred for 10 seconds, heated at 95° C. for 5 min to make a coloring reaction and cooled the reaction mixture with ice water. The resulting solution was centrifuged at 3,000 rpm for 5 min to separate supernatant and measured the absorbance at 540 nm with a UV-visible spectrophotometer. Finally, the amount of malondialdehyde (MDA) generated by the coloring reaction was determined.

On the other hand, the stock solution of tetramethoxypropane[(malon-aldehyde bis(dimethylacetal)] was used to prepare 250 μL of PBS standard solution containing 0-10 nmol of malondialdehyde (MDA). This standard solution was colored by the procedure described above and measured the absorbance at 540 nm. As a result, the standard curve of malondialdehyde was obtained.

In the experiment using *Phellinus* sp. PL3 extract and the phellinsin A isolated from *Phellinus* sp. PL3, the amount of malondialdehyde was quantified by using this standard curve. The results are illustrated in Table 1 as follows.

TABLE 1

Anti-oxidant activities of solvent extracts of culture broth of *Phellinus* sp. PL3

| Solvent extracts | Inhibition (%) |
|---|---|
| MeOH extract of culture broth of *Phellinus* sp. PL3 (Example 3) | 65 |
| MeOH and EtOAc extract of culture broth of *Phellinus* sp. PL3 (Example 4) (280 µg/mL) | 75 |
| EtOAc extract of culture broth of *Phellinus* sp. PL3 (Example 5) (280 µg/mL) | 75 |

* The inhibitory activity at 280 µg/mL of final concentration.

TABLE 2

Anti-oxidant activity of compound phellinsin A to LDL

| Material | $IC_{50}$ (µM) |
|---|---|
| Phellinsin A (Example 6) | 5.3 |
| Probucol (positive control) | 2.2 |

As illustrated in Table 1 and Table 2, the *Phellinus* sp. PL3 extract and the compound phellinsin A isolated from *Phellinus* sp. PL3 of the present invention had the anti-oxidant activity to LDL, but was considered slightly low in $IC_{50}$ value, compared to probucol. Nevertheless, they are proven to be more effective in the anti-oxidation to LDL reaction mediated by conjugated dienes and macrophages than probucol, as described in Experimental Examples 2 and 3. Therefore, the *Phellinus* sp. PL3 extract and phellinsin A derived from the same can be applied usefully to prevent and treat cardiovascular diseases such as hyperlipemia and arteriosclerosis caused by the oxidation of LDL.

Experimental Example 2

Examination of Anti-Oxidant Activity of Compound Phellinsin a by Monitoring Conjugated Dienes Continuously 240 µL of LDL (120 µg/mL of protein concentration) separated in Experimental Example 1 was mixed with 2,510 µL of 10 mM phosphate buffer solution and added with 10 µL of phellinsin A solution prepared in 2 kinds of concentration (2 µM and 5 µM), respectively. At this moment, the phellinsin A was utilized after dissolved in DMSO and for a negative control, only solvent was added. For a positive control, probucol was added before use.

Then, 240 µL of 0.125 mM $CuSO_4$ was added to the resulting solution, reacted at 37° C. for 4 hours and coincidentally, measured by monitoring the absorbance at 234 nm with a UV-visible spectrophotometer at 10 min intervals. The results are summarized in FIG. 1.

As illustrated in FIG. 1, the control group without phellinsin A had a lag time at 44 min; 2 µM of phellinsin A, 192 min; but 5 µM of phellinsin A cannot determine a lag time within 240 min due to a strong inhibitory activity. For a positive control, 2 µM and 5 µM of probucol had lag times at 63 and 70 min, respectively.

Therefore, it is confirmed that the phellinsin A of the present invention may inhibit the generation of conjugated dienes according to the oxidation of LDL in a dose-dependent manner. Further, phellinsin A is delayed the production of conjugated dienes more effectively than probucol used as a positive control.

Experimental Example 3

Examination of Anti-Oxidant Activity of Compound Phellinsin a by Scavenging DPPH Radicals Phellinsin A and 1-diphenyl-2-picryl hydrazyl (DPPH) were dissolved in methanol to be adjusted to 100 µM of concentration, respectively. Then, 1 mL of phellinsin A solution was mixed with 2 mL of DPPH solution and stirred well. The resulting solution was measured the absorbance at 517 nm in a 2 min interval for 30 min. The results are summarized in Table 3.

TABLE 3

DPPH radical scavenger activity of compound phellinsin A

| Compounds | Radical scavenging activity (%) | | |
|---|---|---|---|
| | 5 min | 10 min | 30 min |
| Phellinsin A | 55 | 87 | 92 |
| Probucol | 25 | 53 | 79 |

As illustrated in Table 3, the DPPH radical scavenger activities of phellinsin A and probucol were observed to 92% and 79% at 30 min, respectively. After 35 min, phellinsin A scavenged the DPPH free radical in a dose-dependent manner with an $IC_{50}$ value of 1.7 µM. In contrast, the scavenging activities of trolox, a known DPPH inhibitor, and probucol showed $IC_{50}$ values of 18. 6 µM and 2.2 µM, respectively.

Therefore, it is clarified that the compound phellinsin A of the present invention is excellent in the anti-oxidant activity.

Experimental Example 4

Examination of Anti-Oxidant Activity of Compound Phellinsin a to Macrophage-Mediated LDL THP-1 cells were inoculated into 12-well plate containing RPMI 1640 medium (10% FBS, 5% antibiotic) in $1 \times 10^6$ cells/mL and treated with 150 ng/mL of phobol 12-myristate 13-acetate (PMA). Then, the resulting cells were cultivated for 3 days and activated by using macrophages sufficiently. Then, the culture media were discarded and washed 3 times with RPMI 1640 medium without serum.

84 µL of LDL separated in Experimental Example 1 (100 µg/mL of protein concentration) was mixed with 912 µL of RPMI 1640 medium, dispensed into 12-well plate and added with 2 µL of phellinsin A solution prepared in various concentrations (10 µM, 5 µM, 2 µM and 1 µM), respectively.

Phellinsin A was dissolved in DMSO and diluted in various concentrations before used in the experiment. In order to catalyze the macrophage-mediated LDL oxidation, 2 µL of 0.5 mM $CuSO_4$ was added to the phellinsin A solution. Incubation was then carried out for 24 hours at 37° C. under a humidified atmosphere containing 5% $CO_2$. The resulting supernatant was collected and centrifuged, and finally processed for the measurement of extent of LDL oxidation by the same procedure of TBARS method as described in Experimental Example 1.

The results are summarized in Table 4. As described above, the compound phellinsin A of the present invention is proven to inhibit LDL oxidation in a dose-dependent manner. The anti-oxidant activity of compound phellinsin A was approximately 2-3.7 times stronger than that of probucol, a positive control, on macrophage-mediated LDL oxidation. Therefore, it is confirmed that the compound phellinsin A of the present invention is excellent in the anti-oxidant activity to LDL in a dose-dependent manner.

TABLE 4

Effects of phellinsin A on macrophage-mediated LDL oxidation

| Culture condition | | | MDA nmol/mg LDL protein |
|---|---|---|---|
| LDL + $Cu^{2+}$ | | | 40.2 ± 5.4 |
| LDL + cell + $Cu^{2+}$ (control) | | | 210.6 ± 10.7 |
| LDL + cell + $Cu^{2+}$ | probucol | 1 μM | 209.7 ± 1.7 |
| | | 2 μM | 199.1 ± 10.7 |
| | | 5 μM | 157.4 ± 2.4 |
| | | 10 μM | 145.5 ± 3.9 |
| | Phellinsin A | 1 μM | 167.7 ± 6.2 |
| | | 2 μM | 94.2 ± 4.7 |
| | | 5 μM | 55.9 ± 2.8 |
| | | 10 μM | 39.4 ± 0.9 |

Experimental Example 5

Acute Toxicity Test of Oral Administration in Experimental Mice

In order to investigate the acute toxicity of *Phellinus* sp. PL3 extract or phellinsin A isolated from the same according to the present invention, the experimental procedure is performed as follows.

4-week old specific pathogens free (SPF) ICR mice were adopted in 12 of female and 12 of male mice (3 male and female mice/dose group, respectively) and raised in a breeding room under 12 L/12 D of light kept at temperature of 22±3° C., humidity of 55±10%. The experimental mice were adapted for a week before use. Animal fodder (purchased from Cheil Feed Co. Ltd., for mice and rat uses) and water were provided after sterilized and fed freely.

The *Phellinus* sp. PL3 extract and phellinsin A isolated from the same prepared in Examples were made to 50 mg/mL of concentration by using 0.55% Tween 80 solvent and orally administered in 0.04 mL (100 mg/kg), 0.2 mL (500 mg/kg) and 0.4 mL (1,000 mg/kg) per 20 g of body weight. All the test samples were orally administered once, and then, adverse actions and the fatality were observed for 7 days. In detail, general symptoms and animal deaths were investigated after administration at 1 hour, 4 hours, 8 hours and 12 hours of the day; and then, everyday in the morning and in the afternoon more than once from the next day until the 7th day.

In addition, the experimental mice were killed, anatomized and examined on inner organs with the naked eyes in 7 days of administration. In a day interval from the 1st day, the body weights were measured to examine whether the *Phellinus* sp. PL3 extract and phellinsin A isolated from the same can reduce the body weights of animals.

As a result, it is observed that all the mice administering the test samples does not have any clinical symptoms worth mentioning and are not killed. Further, any toxicity is not detected even in change of body weight, blood test, biochemical test of blood and opinion of autopsy. Therefore, it is confirmed that the *Phellinus* sp. PL3 extract and phellinsin A isolated from the same of the present invention has no toxicity in all the mice until reaching at least 1,000 mg/kg of $LD_{50}$ after oral administration to be safe material.

Practical and presently preferred embodiments of pharmaceutical agent or health food comprising phellinsin A according to the present invention are illustrated as shown in the following Preparative Examples.

However, it will be appreciated that those skilled in the art, on consideration of this disclosure, may make modifications and improvements within the spirit and scope of the present invention.

Preparative Example 1

Preparation of Pharmaceutical Agents

1. Powders
2 g of phellinsin A and 1 g of lactose was mixed and enclosed to prepare the powder.

2. Tablets
100 mg of phellinsin A, 100 mg of cone starch, 100 mg of lactose and 2 mg of magnesium stearic acid were mixed and made to the tablet according to conventional procedures.

3. Capsules
100 mg of phellinsin A, 100 mg of cone starch, 100 mg of lactose and 2 mg of magnesium stearic acid were mixed and enclosed into a gelatin capsule to make the tablet according to conventional procedures.

4. Liquid Injections
10 μg/mL of phellinsin A was dissolved in proper volume of sodium chloride BP for injection use, and adjusted to pH 3.5 by using hydrochloric acid BP. Then, the final volume was adjusted by adding sodium chloride BP for injection use (maximally, 1 mL) and mixed sufficiently. The resulting solution was filled into 5 ml type I ampoule made of transparent glass, dissolved to remove the glass, enclosed under air lattice, and sterilized by autoclaving at 120° C. for more than 15 min to make a liquid injection.

Preparative Example 2

Manufacture of Food

1. Sauces for Cooking
0.2-10 wt % of phellinsin A was utilized to manufacture a functional sauce for cooking improving health.

2. Tomato Ketchups and Sauces
0.2-1.0 wt % of phellinsin A was added to a tomato ketchup or sauce to manufacture a functional tomato ketchup or sauce for cooking improving health.

3. Wheat Flour Foods
0.1-5.0 wt % of phellinsin A was added to a wheat flour and made to a bread, cake, cookie, cracker or noodle by using the mixture to manufacture a functional food improving health.

4. Soups and Gravies
0.1-1.0 wt % of phellinsin A was added to a soup and a gravies to manufacture a functional soup and gravies for meat-processing products and noodles improving health.

5. Ground Beef
10 wt % of phellinsin A was added to a ground beef to manufacture a functional ground beef improving health.

6. Dairy Products
0.1-1.0 wt % of phellinsin A was added to milk to manufacture a functional dairy products such as butter and ice cream by using the milk.

7. Zen Food

Unpolished rice, barley, glutinous rice and adley were made to alpha forms by conventional procedures, dried and pulverized to 60-mesh powder with a grinder. Also, black bean and black sesame and green *perilla* were steamed by conventional procedures and pulverized to 60-mesh powder with a grinder. The compound phellinsin A was concentrated under reduced pressure with a vacuum concentrator, sprayed, dried with a hot-air dryer and pulverized to 60-mesh powder with a grinder to produce a dry powder. The dry powders of crops, seeds and phellinsin A prepared above were mixed in combination comprising crops (unpolished rice 30 wt %, Job's-tears 15 wt %, barley 20 wt %), seeds (green *perilla* 7 wt %, black bean 8 wt %, black sesame 7 wt %), dry powder of phellinsin A (1 wt %) and *Ganoderma lucidum* (0.5 wt %) and *Rehmannia glutinosa* (0.5 wt %).

8. Carbonated Drinks 5-10% of sucrose, 0.05-0.3% of citric acid, 0.005-0.02% of caramel and 0.1-1% of vitamin C were mixed and then 79-94% of purified water to manufacture a syrup. The resulting syrup was sterilized at 85-98° C. for 20-180 seconds and mixed with cooled water in a ratio of 1:4. Then, carbonate gas was injected in 0.5-0.82% to manufacture a functional carbonated drink containing phellinsin A.

9. Health Drinks

The compound phellinsin A and various additives such as liquid fructose (0.5%), oligo-saccharide (2%), sucrose (2%), table salt (0.5%) and water (75%) were mixed uniformly, sterilized instantly, and packaged in a small vessel such as glass bottle and PET bottle to manufacture a functional health drink.

10. Vegetable Juices 0.5 g of phellinsin A was added to 1,000 mL of tomato or carrot juice to manufacture a functional vegetable juice improving health.

11. Fruit Juices 0.1 g of phellinsin A was added to 1,000 mL of apple or grape juice to manufacture a functional fruit juice improving health.

As illustrated and confirmed above, the present invention relates to a pharmaceutical composition and health food comprising *Phellinus* sp. PL3 extract or phellinsin A isolated from the same as an effective component, wherein the *Phellinus* sp. PL3 extract and its phellinsin A inhibit the oxidation of low density lipoprotein (LDL) and further, can be used for medicine and food to prevent and treat cardiovascular diseases such as hyperlipemia and arteriosclerosis.

The pharmaceutical composition and health food comprising *Phellinus* sp. PL3 extract or phellinsin A isolated from the same as an effective component has the anti-oxidant activity and inhibits the generation of conjugated dienes according to the oxidation of LDL and scavenges DPPH radicals more effectively than conventional medicines of liperlipemia such as probucol.

In addition, the antioxidant activity of phellinsin A has about 2-3.7 times stronger than that of probucol according to concentrations, when applying in 2-10 μM. Further, it has no toxicity in all the mice until reaching at least 1,000 mg/kg of $LD_{50}$ after oral administration and thus, is confirmed to be safe material.

All documents mentioned herein are incorporated herein by reference in their entirety.

Even though the present invention is described in detail with reference to the foregoing embodiments, it is not intended to limit the scope of the present invention thereto. It is evident from the foregoing that many variations and modifications may be made by a person having an ordinary skill in the present field without departing from the essential concept of the present invention.

What is claimed is:

1. A method of treating hyperlipidemia or arteriosclerosis comprising administering to a patient in need thereof a pharmaceutical composition a therapeutically effective amount of isolated phellinsin A having a structure of Formula 1:

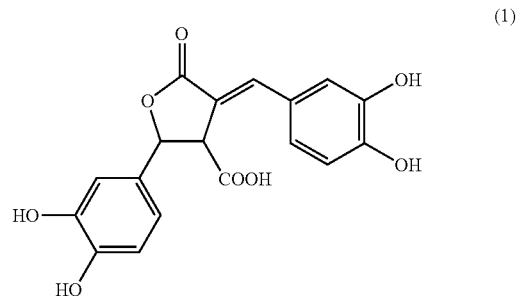

as an active ingredient wherein said phellinsin A is isolated from *Phellinus* sp. PL3.

2. The method according to claim 1, wherein the phellinsin A is used alone itself or in the form of a pharmaceutically acceptable salt, hydroxides or solvated compounds thereof.

3. The method according to claim 1, wherein the composition further comprises one or more of pharmaceutically acceptable carrier.

4. The method according to claim 1, wherein the carrier is selected from the group consisting of saline, sterilized water, Ringer's solution, buffered saline, dextrose solution, maltodextrin solution, glycerin and ethanol.

5. The method according to claim 1, wherein the composition further comprises an additive selected from the group consisting of anti-oxidant, a buffer solution and an anti-fungal agent.

6. The method according to claim 1, wherein the composition further comprises a diluent, a dispersing agent, a surfactant, a binder or a lubricant.

7. The method according to claim 1, wherein the composition is parenterally administered or orally administered.

8. The method according to claim 1, wherein the composition is administered alone or in combination with surgery, hormone treatment, a drug or a biological controller.

9. The method of claim 1, wherein the isolation of phellinsin A is isolated from *Phellinus* sp. PL3 by using a mixed solvent of chloroform, methanol and acetone in a ratio of 85-90: 7-8: 2-3% (v/v).

10. The method of claim 9, wherein the mixed solvent of chloroform, methanol and acetone are in a ratio of 90: 7.5: 2.5% (v/v).

11. The method of claim 9, wherein the isolation by a mixed solvent is followed by a separation by high performance liquid chromatography using a methanol-water mixture as an eluent wherein the ratio of methanol to water is in the range of 30:70 to 20:80 (v/v).

12. The method of claim 11, wherein the method of treatment is for hyperlipidemia.

13. The method of claim 11, wherein the method of treatment is for arteriosclerosis.

* * * * *